US006506931B1

(12) United States Patent
Ishibashi et al.

(10) Patent No.: US 6,506,931 B1
(45) Date of Patent: Jan. 14, 2003

(54) PROCESS FOR PRODUCING AROMATIC CARBOXYLIC ACID

(75) Inventors: Masayasu Ishibashi, Kuma-Gun (JP); Hiroshi Tomita, Kuga-Gun (JP)

(73) Assignee: Mitsui Chemicals, Inc., Tokyo (JP)

( * ) Notice: Subject to any disclaimer, the term of this patent is extended or adjusted under 35 U.S.C. 154(b) by 0 days.

(21) Appl. No.: 09/656,997

(22) Filed: Sep. 7, 2000

(30) Foreign Application Priority Data

Sep. 7, 1999 (JP) ............................................. 11-252941

(51) Int. Cl.⁷ ............................................. C07C 51/255
(52) U.S. Cl. ....................................... 562/412; 562/414
(58) Field of Search .................................. 562/412, 414

(56) References Cited

FOREIGN PATENT DOCUMENTS

JP A258121244 7/1983

Primary Examiner—Johann Richter
Assistant Examiner—Paul A. Zucker
(74) Attorney, Agent, or Firm—Birch Stewart Kolasch & Birch LLP

(57) ABSTRACT

A process for producing an aromatic carboxylic acid by a liquid phase oxidation of an alkylaromatic compound with molecular oxygen in a reaction solvent comprising a lower aliphatic carboxylic acid in the presence of an oxidation catalyst, in which an aromatic carboxylic acid having an improved hue of the powdery product thereof and exhibiting an improved light transmittance when dissolved in an aqueous solution of a base can be produced efficiently in a simple manner by suppressing contamination due to the intermediates and by-products formed by side reactions, the said process comprising performing the liquid phase oxidation of the alkylaromatic compound in the presence of a hydrogen gas-treated liquid containing the catalyst.

5 Claims, 1 Drawing Sheet

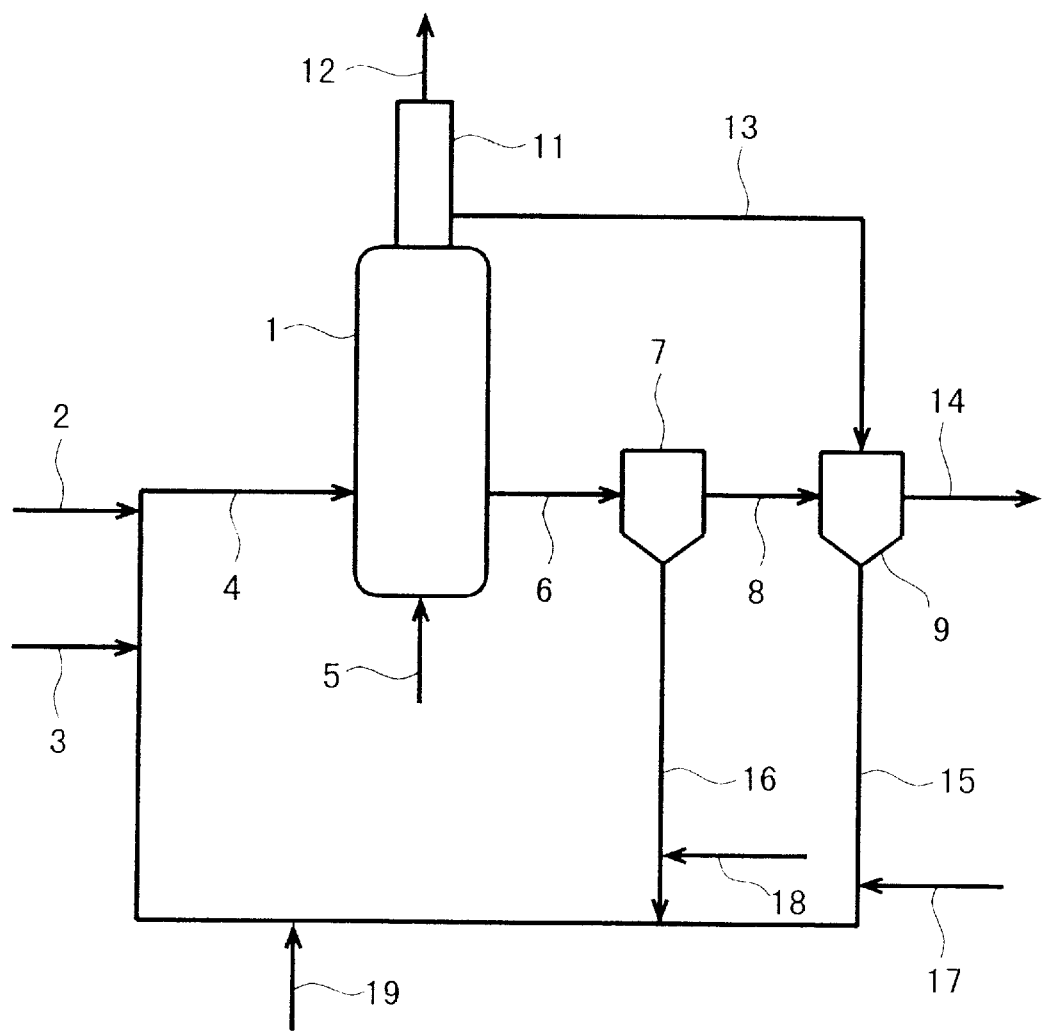

PROCESS FOR PRODUCING AROMATIC CARBOXYLIC ACID

FIELD OF THE INVENTION

The present invention relates to a process for producing an aromatic carboxylic acid, which is suitable especially for producing terephthalic acid, by subjecting an alkylaromatic compound to a liquid phase oxidation with molecular oxygen.

BACKGROUND OF THE INVENTION

Heretofore, an aromatic carboxylic acid, such as terephthalic acid, has been industrially produced in a large scale by a process comprising subjecting an alkylbenzene such as para-xylene, to a liquid phase oxidation in a reaction solvent containing a lower aliphatic carboxylic acid, such as acetic acid, with molecular oxygen in the presence of a catalyst constituted of a combination composed of a compound of a heavy metal, such as cobalt, manganese or the like, and a bromine compound.

When an aromatic carboxylic acid is produced in this production process, the quality of the resulting aromatic carboxylic acid is debased due to inclusion of the intermediates and contamination by impurities formed by side reactions and, in particular, large debasements occur in the hue of the powdery product thereof and in the light transmittance when it is dissolved in an aqueous solution of a base.

BRIEF SUMMARY OF THE INVENTION

The object of the present invention is to provide a process for producing an aromatic carboxylic acid, in which an aromatic carboxylic acid having a low content of 4-carboxybenzaldehyde (4-CBA) and an improved hue of the powdery product thereof and exhibiting an improved light transmittance when dissolved in an aqueous solution of a base can be produced efficiently in a simple manner.

The present invention resides in the following process for producing an aromatic carboxylic acid:

(1) A process for producing an aromatic carboxylic acid by a liquid phase oxidation of an alkylaromatic compound with molecular oxygen in a reaction solvent comprising a lower aliphatic carboxylic acid in the presence of an oxidation catalyst, comprising performing the liquid phase oxidation of the alkylaromatic compound in the presence of a hydrogen gas-treated liquid containing the catalyst.

(2) The process as defined in the above (1), wherein the oxidation catalyst is constituted of a combination of a heavy metal compound and a bromine compound.

(3) The process as defined in the above (1) or (2), wherein the hydrogen gas-treated liquid is one, in which the reaction solvent containing the catalyst held in a state dissolved or dispersed therein is treated with hydrogen gas.

(4) The process as defined in any one of the above (1) to (3), wherein the amount of the hydrogen gas to be used in the treatment with hydrogen gas is 0.000001–0.05 N liter per one gram of the total sum of the reaction solvent plus the catalyst to be introduced into the oxidation reaction step.

(5) The process as defined in any one of the above (1) to (4), wherein the aromatic carboxylic acid is terephthalic acid.

BRIEF DESCRIPTION OF THE DRAWINGS

FIG. 1 shows a schematic flow diagram of one embodiment of the process according to the present invention.

DETAILED DESCRIPTION OF THE INVENTION

The alkylaromatic compound (in the following, referred to sometimes simply as "the raw material") used for producing the aromatic carboxylic acid according to the present invention is an aromatic compound having one or more substituent alkyl groups, wherein part of the occasionally existing two or more functional groups may be an oxidized alkyl group. Such alkylaromatic compounds may be monocyclic or polycyclic. While the compound may have one single such alkyl-containing functional group, it may preferably have two or more such substituent groups.

As the substituent alkyl group, there may be mentioned, for example, alkyl groups having 1–4 carbon atoms, such as methyl, ethyl, n-propyl and isopropyl. As the oxidized alkyl group, there may be mentioned, for example, formyl, acyls, carboxyl and hydroxyalkyls.

As the concrete examples of the alkylaromatic compound, there may preferably be mentioned di- and polyalkylbenzenes having 2–4 alkyl groups of 1–4 carbon atoms, such as m-diisopropylbenzene, p-diisopropylbenzene, m-cymene, p-cymene, m-xylene, p-xylene, trimethylbenzenes and tetramethylbenzene; di- and polyalkylnaphthalenes having 2–4 alkyl groups of 1–4 carbon atoms, such as dimethylnaphthalenes, diethylnaphthalenes and diisopropylnaphthalenes; and polyalkylbiphenyls, having 2–4 alkyl groups of 1–4 carbon atoms, such as dimethylbiphenyls. They may be employed either alone or in a combination of two or more of them.

As the concrete examples of the alkylaromatic compound having partly oxidized substituent alkyl group, there may be mentioned 3-methylbenzaldehyde, 4-methylbenzaldehyde, m-toluic acid, p-toluic acid, 3-formylbenzoic acid, 4-formylbenzoic acid, 2-methyl-6-formylnaphthalene and formylnaphthalenecarboxylic acid. They may be employed either alone or in a combination of two or more of them.

The aromatic compound having alkyl substituent group may be combined with the aromatic compound having partially oxidized alkyl group to use as the production raw material.

The reaction solvent to be used in the process according to the present invention comprises a lower aliphatic carboxylic acid. As the lower aliphatic carboxylic acid, those having 6 or less carbon atoms may favorably be employed with preference to those having 2–3 carbon atoms. As the concrete examples of such a lower aliphatic carboxylic acid, there may be mentioned acetic acid, propionic acid, butyric acid and isobutyric acid.

The reaction solvent may consist of individual lower aliphatic carboxylic acid alone or of a mixture with one or more other lower aliphatic carboxylic acids or with water. Above all, acetic acid alone or a mixture of acetic acid with water is preferred.

On using a mixture of acetic acid with water as the reaction solvent, the water content may preferably be not higher than 20% by weight.

The reaction solvent comprising the lower aliphatic carboxylic acid may favorably be used in a proportion of 1–20 parts by weight, preferably 2–10 parts by weight, per one part by weight of the alkylaromatic compound to be used as the production raw material.

The oxidation reaction in the process according to the present invention is carried out in the presence of an oxidation catalyst. As the oxidation catalyst, any one constituted of combination of a heavy metal compound and a bromine compound soluble both in the reaction solvent may favorably be used, though there is no special restriction.

As the heavy metal for the heavy metal compound, there may be mentioned, for example, cobalt, manganese, nickel, chromium, zirconium, copper, lead, hafnium and cerium. They may be used either alone or in combination.

As the heavy metal compound, there may be mentioned, for example, bromides, acetates, nitrates, acetylacetonato complexes, naphthenates, stearates and benzoates of these heavy metals, with special preference to the acetates and bromides.

As the bromine compound, there may be mentioned, for example, inorganic bromine compounds, such as molecular bromine, hydrogen bromide, sodium bromide, potassium bromide, ammonium bromide, cobalt bromide and manganese bromide; and organic bromine compounds, such as methylene bromide, bromoform, tetrabromomethane, benzyl bromide, bromomethyltoluene, bromomethylbenzoic acid, dibromoethane, tribromoethane, tetrabromoethane and N-bromosuccinimide. They also may be used either alone or in a combination of two or more of them.

In the production process according to the present invention, the oxidation catalyst constituted of combination of the heavy metal compound and the bromine compound may favorably be in an atomic proportion in the range from 0.05 to 10 gram-atoms of bromine per one gram-atom of the heavy metal, preferably in the range from 0.1 to 2 gram-atoms per one gram-atom of the heavy metal. The catalyst may usually be employed, as metal atom concentration in the reaction solvent, in an amount in the range from 10 to 5,000 ppm, preferably from 100 to 5,000 ppm, and, as bromine atom concentration in the reaction solvent, in the range from 10 to 10,000 ppm, preferably from 100 to 5,000 ppm.

For molecular oxygen for effecting the liquid phase oxidation of the alkylaromatic compound as the raw material in the reaction solvent, there may be employed a molecular oxygen-containing gas, such as pure oxygen, atmospheric air, oxygen-enriched air or a mixture of oxygen with an inert gas. The oxidation reaction is performed while supplying molecular oxygen in excess of the stoichiometry of oxidation of the alkylaromatic compound into the aromatic carboxylic acid. In oxidizing paraxylene, the molecular oxygen-containing gas may be supplied to the oxidation reaction in such an amount that 0.1–3 $Nm^3$ (converted into the volume at 0° C., 1 atm.) of oxygen is supplied thereto per 1 kg of para-xylene. In the case of using atmospheric air as the molecular oxygen-containing gas, it is supplied to the oxidation reactor preferably in an amount of 0.5 to 15 $Nm^3$ per 1 kg of para-xylene.

In performing the liquid phase oxidation of an alkylaromatic compound as the raw material with molecular oxygen in a reaction solvent comprising a lower aliphatic carboxylic acid in the production process according to the present invention, the oxidation reaction is carried out in the presence of a hydrogen gas-treated liquid containing the catalyst, in order to improve the hue of the resulting powdery product of the aromatic carboxylic acid crystals and to improve the light transmittance of a solution of the aromatic carboxylic acid dissolved in an aqueous solution of a base. As the liquid to be subjected to the hydrogen gas-treatment, there may be mentioned a liquid mixture composed of the reaction solvent with the catalyst and/or the raw material admixed thereto, the reaction solvent as such, the mother liquor of the reaction mixture freed from the aromatic carboxylic acid formed and even the raw material itself. The liquid to be hydrogen gas-treated may favorably be subjected to the hydrogen gas-treatment before being introduced into the oxidation reaction. It may be hydrogen gas-treated together with the catalyst contained therein. When the liquid without the catalyst is hydrogen gas-treated, the so-treated liquid may be introduced into the oxidation reaction together with the catalyst admixed thereto.

The hydrogen gas-treatment is effected by contacting the liquid to be hydrogen gas-treated with gaseous hydrogen. Here, the catalyst may be present therein in a state of solid, liquid or dispersion. It is possible to contact only the reaction solvent with hydrogen gas, while it is also possible to contact a liquid containing the catalyst in a dissolved or dispersed form or even a mixture of such a liquid and the raw material with hydrogen gas. In case the mother liquor of the slurry of reaction mixture containing the reaction product is reused for the oxidation reaction after having been freed from the reaction product, the hydrogen gas-treatment may be effected for the mother liquor containing the spent catalyst or for the mixture of the mother liquor with freshly added catalyst. In case the reaction solvent is recovered from the oxidation exhaust gas and reused for the oxidation reaction, the hydrogen gas-treatment may be effected for the recovered solvent or for the spent washing liquor resulting from washing of the crude aromatic carboxylic acid crystals with the recovered solvent.

A practical method for effecting the hydrogen gas-treatment may consist in bubbling of hydrogen gas or hydrogen-containing gas mixture into the liquid to be hydrogen gas-treated, such as the reaction solvent or the catalyst-containing liquid or slurry. The bubbling may be effected in a vessel or in a liquid line by pure hydrogen gas, by a gas mixture of hydrogen gas with an inert gas, such as nitrogen or argon, or even by a gas mixture of hydrogen gas with air.

The amount of the hydrogen gas to be used may favorably be 0.000001–0.05 N liter, preferably 0.000005 to 0.02 N liter, per one gram of the total sum of the reaction solvent plus the catalyst to be introduced into the oxidation reaction step.

The hydrogen gas contact may be effected at a temperature in the range of 25–250° C., preferably 25–200° C., under a pressure in the range from the atmospheric pressure to the pressure of the oxidation reaction, wherein the contacting treatment may usually be attained enough at normal temperature under the atmospheric pressure.

For performing the process for producing an aromatic caboxylic acid according to the present invention, the oxidation reactor is supplied with the alkylaromatic compound as the raw material, the reaction solvent consisting of or comprising a lower aliphatic carboxylic acid and the catalyst, while supplying thereto molecular oxygen-containing gas, to effect the oxidation reaction. The hydrogen gas-treatment of the raw material, the reaction solvent and the catalyst solution may be carried out either before or after they are introduced into the reactor. The oxidation reaction may favorably be realized at a temperature in the range from 160 to 260° C., preferably from 170 to 220° C., under a pressure in the range from 0.4 to 5 MPa (gauge), preferably from 0.5 to 2 MPa (gauge), for a reaction duration in the range from 10 to 200 minutes, preferably from 30 to 120 minutes. The reaction may be effected in any voluntary way, such as in a continuous, batch-wise or other way. The molecular oxygen-containing gas may be supplied in a once-through principle, though the oxidation reaction may also be realized by recirculating a large proportion of the oxidation exhaust gas while discarding some of it.

By performing the reaction in the manner as above, the alkylaromatic compound used as the raw material is oxidized into an aromatic carboxylic acid corresponding to each specific raw material used. Concrete examples of the aromatic carboxylic acid include aromatic dicarboxylic acids, such as terephthalic acid, isophthalic acid, 2,6-naphthalene dicarboxylic acid and 4,4'-biphenyl dicarboxylic acid; aromatic tricarboxylic acid, such as trimellitic acid and trimesic acid; and aromatic polycarboxylic acids, such as pyromellitic acid.

The production process according to the present invention may favorably be applied for producing an aromatic carboxylic acid insoluble or difficultly soluble in the reaction solvent, in particular, for producing terephthalic acid.

The reaction liquor containing the aromatic carboxylic acid formed by the oxidation reaction is withdrawn from the oxidation reactor and is subjected to a solid/liquid separation by a conventional technique, such as filtration or centrifugation. The so-separated aromatic carboxylic acid is then washed and dried, followed by, if necessary, a purification by a known practice. The separated mother liquor can be reused for the oxidation reaction as the catalyst-containing reaction solvent, while it is also possible to subject the mother liquor to the hydrogen gas-treatment for preparing the hydrogen gas-treated liquid containing the catalyst which can be supplied to the oxidation reactor. When the reaction solvent is recovered from the oxidation exhaust gas by distillation, the hydrogen gas-treated liquid containing the catalyst may be prepared also by subjecting the recovered reaction solvent, or the spent washing liquor resulting from washing the crude aromatic carboxylic acid crystals with the recovered reaction solvent, to the hydrogen gas-treatment and mixing the resulting hydrogen gas-treated liquor with the mother liquor.

By the process for producing an aromatic carboxylic acid according to the present invention, the content of the intermediate, 4-CBA, in the resulting product is reduced and the by-production of substances formed by side-reactions are suppressed, since the conversion of the intermediate into the aromatic carboxylic acid is facilitated by the liquid phase oxidation of an alkylaromatic compound in the presence of a hydrogen gas-treated liquid containing the oxidation catalyst, whereby an aromatic carboxylic acid of which the hue of the powdery produt is improved and the light transmittance when dissolved in an aqueous solution of a base is improved can be produced in a simple and efficient manner.

Below, the present invention will be described by way of embodiments with reference to the drawings appended.

In FIG. 1, a flow diagram for one embodiment of the process is shown, in which the process according to the present invention is applied for producing terephthalic acid.

As shown in FIG. 1, the oxidation reactor 1 is supplied with para-xylene as the raw material via a line 2, with the catalyst constituted of a cobalt compound, a manganese compound and a bromine compound via a line 3 and with acetic acid as the reaction solvent via a line 4, while supplying thereto atmospheric air via a line 5, to effect the oxidation in order to form terephthalic acid. The slurry containing the resulting terephthalic acid crystals in the oxidation reactor 1 is taken out via a line 6 into a solid/liquid separator 7, where it is subjected to a solid/liquid separation, wherein the crystals separated are transferred via a line 8 to a washing vessel 9.

On the other hand, the oxidation exhaust gas from the oxidation reactor 1 is subjected to a distillation in a distillation column 11, from which the residual gas is discharged out via a line 12 and the recovered acetic acid is sent to the washing vessel 9 via a line 13 and is used, together with a make-up solvent, for washing the crude crystals. In the washing vessel 9, the crude crystals are washed with the reaction solvent to remove the catalyst residue and other impurities adhering on the crystal surfaces and the so-washed terephthalic acid crystals are taken out of the washing vessel 9 via a line 14 as a primary product. The spent washing liquor is discharged out of the washing vessel 9 via a line 15 and is mixed with the mother liquor drawn via a line 16 and the mixture is supplied to the oxidation reactor 1 through the line 4 to use as the reaction solvent.

In such a system, according to the present invention, the oxidation reaction is carried out in the presence of a hydrogen gas-treated liquid containing the catalyst, wherein the hydrogen gas-treatment may favorably be effected by introducing hydrogen gas into a line, such as a line 17, 18 or 19. When introducing hydrogen gas into line 17, the hydrogen gas-treatment may be effected for the spent washing liquor consisting predominatly of the raction solvent and the resulting hydrogen gas-treated liquid is supplied to the oxidation reactor 1 as the hydrogen gas-treated liquid containing the catalyst, after being mixed with the mother liquor containing the catalyst, in order to carry out the oxidation reaction. When introducing hydrogen gas into line 18, the hydrogen gas-treatment is realized for the mother liquor containing the catalyst and the reaction solvent and the resulting hydrogen gas-treated liquid is supplied to the oxidizing reactor 1 after being mixed with the spent washing liquor containing the reaction solvent, in order to carry out the oxidation reaction. When introducing hydrogen gas into line 19, the hydrogen gas-treatment is effected for the mixed liquid of the mother liquor and the spent washing liquor and the resulting hydrogen gas-treated liquid is supplied to the oxidation reactor 1, in order to carry out the oxidation.

The hydrogen gas may be supplied to the system at another place and may be introduced into the system not in a line but at any other location, such as by vessels or the like. The hydrogen gas-treatment may also be realized by introducing hydrogen gas into the oxidation reactor 1 when the operation of the system begins.

EXAMPLES

Below, the present invention will be described by way of Examples, wherein it is to be noted that the present invention is not restricted by such Examples.

The determinations of the hue of the powdery product of terephthalic acid obtained in each Examples and of the light transmittance of the aqueous solution prepared by dissolving the powdery terephthalic acid in an aqueous solution of a base were carried out in the manner as given below:

○ Hue (b-value) of powdery terephthalic acid:

The value was determined using a color computer of model SM-6CH of the firm SUGA Shikenki.

○ Light transmittance of a solution in an aq. base:

Light transmittance at a wave length of 340 nm was determined for a solution in an aqueous base prepared by dissolving 7.50 grams of a powdery product of terephthalic acid in 50 ml of an aqueous solution of 2 M potassium hydroxide using model UV-160A spectrophotometer of Shimazu Corporation.

EXAMPLE 1

In a pressure reactor made of titanium and equipped with a reflux condenser, a stirrer, a heating device, a feed line for para-xylene, an air introduction tube, a hydrogen introduction tube and an exhaust gas discharge pipe, there were charged 214 grams of acetic acid containing 5.84% by weight of water, 0.54 gram of cobalt acetate tetrahydrate, 0.26 gram of manganese acetate tetrahydrate and 0.34 gram of aqueous solution of hydrobromic acid (47% aq. Solution) and the internal pressure was adjusted at 1.3 Mpa, while supplying thereto 1.5 N liters per minute of nitrogen gas. Hydrogen gas was supplied thereto at a rate of 0.2 N liter per minute for 10 minutes at a temperature of the oxidation catalyst solution of 25° C., while passing nitrogen gas thereto. Then, the supply of hydrogen gas was stopped and the contents were heated at 170° C. Then, para-xylene was introduced thereinto at a feed rate of 40.3 grams per hour while supplying thereto atmospheric air at a supply rate of 0.168 N m$^3$ per hour, to effect the reaction at a temperature of 190° C. for an hour to produce terephthalic acid. The hue of the resulting terephthalic acid powdery product, the light transmittance value and the content of the impurity, 4-carboxybenzaldehyde (4-CBA), are recited in Table 1.

EXAMPLE 2

In the same manner as in Example 1, except that the temperature upon contact with hydrogen gas was changed to 150° C., terephthalic acid was produced. The results are recited in Table 1.

EXAMPLE 3

In the same manner as in Example 1, except that the supply of hydrogen gas was changed to 0.2 N liter per minute for 2 minutes, terephthalic acid was produced. The results are recited in Table 1.

EXAMPLE 4

In the same manner as in Example 3, except that the pressure of hydrogen supplied was changed to the atmospheric pressure and the nitrogen gas supply was stopped, terephthalic acid was produced. The results are recited in Table 1.

EXAMPLE 5

In the same manner as in Example 4, except that the supply of hydrogen gas was changed to 0.2 N liter/min. for 0.5 minute, terephthalic acid was produced. The results are recited in Table 1.

EXAMPLE 6

215 grams of the oxidation mother liquor to be recirculated to the oxidation of para-xylene in a terephthalic acid production plant were charged to the reactor of Example 1, whereto 0.2 N liter of hydrogen gas was supplied at room temperature under atmospheric pressure. The contents were heated up to 170° C. while bubbling nitrogen gas thereinto. Para-xylene was supplied to the reactor at a rate of 40.3 grams per hour, while passing atmospheric air thereto at a feed rate of 0.168 N m$^3$ per hour, to effect the reaction at a temperature of 190° C. for one hour to produce terephthalic acid.

The hue of the resulting terephthalic acid product, the light transmittance value and the content of the impurity, 4-carboxybenzaldehyde (4-CBA), are recited in Table 1.

EXAMPLE 7

To a solution of 0.54 gram of cobalt acetate and 150 grams of acetic acid, 0.4 N liter of hydrogen gas was supplied over a period of 2 minutes, whereupon nitrogen gas was bubbled thereto for three minutes. The solution was replenished with further components to formulate the oxidation catalyst solution composition of Example 1, whereupon the oxidation of para-xylene was carried out. The results are recited in Table 1.

EXAMPLE 8

Terephthalic acid was produced in the same manner as in Example 7, except that 0.54 gram of cobalt acetate and 0.26 gram of manganese acetate were charged in the reactor. The results are recited in Table 1.

EXAMPLE 9

Terephthalic acid was produced in the same manner as in Example 7, except that 0.54 gram of cobalt acetate and 0.34 gram of hydrobromic acid (47% aqueous solution) were charged in the reactor. The results are recited in Table 1.

EXAMPLE 10

Terephthalic acid was produced in the same manner as in Example 7, except that 0.34 gram of hydrobromic acid (47% aqueous solution) was charged in the reactor. The results are recited in Table 1.

Comparative Example 1

Terephthalic acid was produced in the same manner as in Example 1, except that hydrogen gas was not supplied. The results are recited in Table 1.

Comparative Example 2

Terephthalic acid was produced in the same manner as in Example 6, except that hydrogen gas was not supplied and atmospheric air was supplied at a feed rate of 0.168 N m$^3$ per hour to effect the reaction at a temperature of 190° C. The results are recited in Table 1.

TABLE 1

| Example or Compar. Example | Hydrogen gas treatment | | | 4-CBA content (ppm) | Hue b-value | Light transmit. T-340 (%) | CO$_x$ conc. in waste gas (%) |
| --- | --- | --- | --- | --- | --- | --- | --- |
| | H$_2$ fed (Nl) | Temp. (° C.) | Press. (MPa) | | | | |
| Example | | | | | | | |
| 1 | 2 | R.T.[1)] | 1.3 | 2520 | 8.3 | 5.7 | 1.72 |
| 2 | 2 | 150 | 1.3 | 2440 | 7.6 | 9.9 | 1.75 |
| 3 | 0.4 | R.T. | 1.3 | 2250 | 6.5 | 23.8 | 1.80 |

TABLE 1-continued

| Example or Compar. Example | Hydrogen gas treatment | | | 4-CBA | | Light transmit. | CO$_x$ conc. in waste |
|---|---|---|---|---|---|---|---|
| | H$_2$ fed (Nl) | Temp. (° C.) | Press. (MPa) | content (ppm) | Hue b-value | T-340 (%) | gas (%) |
| 4 | 0.4 | R.T. | N.P.[2)] | 2010 | 6.3 | 24.2 | 1.80 |
| 5 | 0.1 | R.T. | N.P. | 2330 | 7.1 | 11.3 | 1.75 |
| 6 | 0.2 | R.T. | N.P. | 2400 | 8.7 | 7.8 | 2.05 |
| 7 | 0.4 | R.T. | N.P. | 2600 | 8.6 | 3.5 | 1.75 |
| 8 | 0.4 | R.T. | N.P. | 2570 | 8.3 | 4.1 | 1.85 |
| 9 | 0.4 | R.T. | N.P. | 2410 | 6.9 | 11.5 | 1.80 |
| 10 | 0.4 | R.T. | N.P. | 2310 | 5.5 | 23.3 | 1.75 |
| Comp. Ex. | | | | | | | |
| 1 | — | — | — | 3120 | 10.2 | 1.0 | 1.70 |
| 2 | — | — | — | 3160 | 9.9 | 1.2 | 2.05 |

Notes:
[1)]Room temperature
[2)]Normal pressure

EXAMPLE 11

215 grams of a liquid mixture of the mother liquor and the recovered solvent to be recirculated to the oxidation of para-xylene in a terephthalic acid production plant were subjected to the hydrogen gas-treatment by supplying thereto hydrogen gas at a feed rate of 0.2 N liter per minute for 6 seconds with agitation. The dissolved amount of hydrogen gas in the liquid to be treated at room temperature was 0.5 volume %. The mixed liquid through which hydrogen gas was passed was charged in an oxidizing reactor and was heated at 170° C. while bubbling nitrogen gas thereinto. The nitrogen gas bubbling was stopped and para-xylene was supplied to the reactor at a rate of 40.3 grams per hour, while passing atmospheric air thereto at a feed rate of 0.168 N m$^3$ per hour, to effect the reaction at a temperature of 186° C. for one hour to produce terephthalic acid. The hue of the resulting terephthalic acid product, the light transmittance value and the content of the impurity, 4-CBA, are recited in Table 2.

EXAMPLE 12

Terephthalic acid was produced in the same manner as in Example 11, except that the amount of hydrogen gas supplied was changed to 0.2 N liter per minute for 30 seconds and the dissolved amount of hydrogen gas in the liquid to be treated was found to be 1.4 volume %. The results are recited in Table 2.

EXAMPLE 13

Terephthalic acid was produced in the same manner as in Example 11, except that the amount of hydrogen gas supplied was changed to 0.2 N liter per minute for 40 seconds and the dissolved amount of hydrogen gas in the liquid to be treated was found to be 2.0 volume %. The results are recited in Table 2.

EXAMPLE 14

Terephthalic acid was produced in the same manner as in Example 11. Except that the amount of hydrogen gas supplied was changed to 0.2 N liter per minute for 1 minute and the dissolved amount of hydrogen gas in the liquid to be treated was found to be 3.5 volume %. The results are recited in Table 2.

Comparative Example 3

The procedures of Example 11 were pursued, except that hydrogen gas was not supplied. The results are recited in Table 2.

TABLE 2

| Example or Compar. Example | H$_2$ fed (Nl) | 4-CBA cont. (ppm) | Hue (b-value) | Light transm. T-340 (%) | Waste gas CO$_x$ conc. (%) |
|---|---|---|---|---|---|
| Example | | | | | |
| 11 | 0.02 | 3,000 | 6.4 | 11.2 | 1.90 |
| 12 | 0.10 | 2,900 | 7.0 | 18.5 | 1.90 |
| 13 | 0.13 | 3,100 | 6.4 | 13.3 | 1.90 |
| 14 | 0.20 | 3,600 | 6.9 | 12.8 | 1.90 |
| C. Exam. 3 | 0 | 3,700 | 7.2 | 2.2 | 1.90 |

EXAMPLE 15

In an oxidation reactor, there were charged 211.9 grams of a hydrogen gas-treated liquid obtained by passing, with agitation, hydrogen gas to 250 ml of acetic acid containing 4.9% by weight of water at a feed rate of 0.2 N liter per minute for 10 seconds and a catalyst solution obtained from 2.89 grams of an aqueous solution containing 18.7% by weight of cobalt acetate tetrahydrate and 9.3% by weight of manganese acetate tetrahydrate and from 0.44 grams of a 47% conc. aqueous solution of HBr and the contents of the reactor were heated up to 170° C. while bubbling nitrogen gas thereinto. The nitrogen gas bubbling was stopped and para-xylene was introduced into the reactor at a feed rate of 40.3 grams per hour, while at the same time introducing atmospheric air thereinto at a feed rate of 0.168 N m$^3$ per hour, to effect the oxidation at 186° C. for one hour to produce terephthalic acid. The hue of the resulting terephthalic acid product, the light transmittance value and the content of the impurity, 4-CBA, are recited in Table 3.

Comparative Example 4

Terephthalic acid was produced in the same manner as in Example 15, except that hydrogen gas was not supplied to the acetic acid solution. The results are recited in Table 3.

TABLE 3

| Example or Compar. Example | H₂ fed (Nl) | 4-CBA cont. (ppm) | Hue (b-value) | Light transm. T-340 (%) | Waste gas CO$_x$ conc. (%) |
|---|---|---|---|---|---|
| Example 15 | 0.033 | 3,000 | 8.5 | 2.0 | 1.70 |
| C. Ex. 4 | 0 | 3,400 | 9.2 | 1.3 | 1.68 |

EXAMPLE 16

107.5 grams of the mother liquor separated by filtration from the reaction mixture withdrawn from the para-xylene oxidation reactor in a terephthalic acid production plant and 107.5 grams of a treated spent washing liquor obtained by passing hydrogen gas at a feed rate of 0.2 N liter per minute for 10 seconds to 175 ml of the used washing liquor obtained when the reaction product freed from the mother liquor was washed with recovered acetic acid or with fresh acetic acid were mixed together and the resulting mixture was charged in the oxidation reactor, in order to produce terephthalic acid by the oxidation procedure as in Example 15. The results are recited in Table 4.

Comparative Example 5

Terephthalic acid was produced in the same manner as in Example 16, except that hydrogen gas was not supplied to the spent washing liquor. The results are recited in Table 4.

TABLE 4

| Example or Compar. Example | H₂ fed (Nl) | 4-CBA cont. (ppm) | Hue (b-value) | Light transm. T-340 (%) | Waste gas CO$_x$ conc. (%) |
|---|---|---|---|---|---|
| Example 16 | 0.033 | 4,100 | 5.8 | 15.1 | 1.70 |
| C. Ex. 5 | 0 | 4,500 | 6.2 | 19.7 | 1.70 |

What is claimed is:

1. A process for producing an aromatic carboxylic acid by a liquid phase oxidation of an alkylaromatic compound with molecular oxygen in a reaction solvent comprising a lower aliphatic carboxylic acid in the presence of an oxidation catalyst, comprising performing the liquid phase oxidation of the alkylaromatic compound in the presence of a hydrogen gas-treated liquid containing the oxidation catalyst, wherein the hydrogen gas-treated liquid is at least one selected from the group consisting of a liquid mixture composed of the reaction solvent and the oxidation catalyst and/or the alkylaromatic compound admixed thereto, the reaction solvent, a mother liquor obtained from a reaction mixture by removing the aromatic carboxylic acid formed and the alkylaromatic compound itself.

2. The process as claimed in claim 1, wherein the oxidation catalyst contains a combination of a heavy metal compound and a bromine compound.

3. The process as claimed in claim 1 or 2, wherein the hydrogen gas-treated liquid is one, in which the reaction solvent containing the catalyst held in a state dissolved or dispersed therein is treated with hydrogen gas.

4. The process as claimed in claim 1, wherein the liquid that is treated with hydrogen gas is treated with 0.000001–0.05 N liter of hydrogen gas per one gram of the total sum weight of the reaction solvent plus the oxidation catalyst present in the oxidation reaction step.

5. The process as claimed in any one of claim 1, wherein the aromatic carboxylic acid is terephthalic acid.

* * * * *

UNITED STATES PATENT AND TRADEMARK OFFICE
CERTIFICATE OF CORRECTION

PATENT NO.   : 6,506,931 B1                                                                                 Page 1 of 1
DATED        : January 14, 2003
INVENTOR(S)  : Masayasu Ishibashi and Hiroshi Tomita It is certified that error appears in the above-identified patent and that said Letters Patent is hereby corrected as shown below:

<u>Column 12,</u>
Lines 36 and 37, please correct claim 5 as follows:
Change from: "5. The process as claimed in any one of claim 1, wherein the aromatic carboxylic acid is terephthalic acid."

to:   -- 5. The process as claimed in claim 1, wherein the aromatic carboxylic acid is terephthalic acid. --

Signed and Sealed this

Twenty-fourth Day of June, 2003

JAMES E. ROGAN
*Director of the United States Patent and Trademark Office*